US007265171B2

(12) United States Patent
Leppard et al.

(10) Patent No.: US 7,265,171 B2
(45) Date of Patent: Sep. 4, 2007

(54) TRANSPARENT POLYMER ARTICLES OF LOW THICKNESS

(75) Inventors: David George Leppard, Marly (CH); François Gugumus, Allschwil (CH); Michela Bonora, Bologna (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/359,228

(22) Filed: Feb. 22, 2006

(65) Prior Publication Data

US 2006/0141207 A1    Jun. 29, 2006

Related U.S. Application Data

(63) Continuation of application No. 10/894,773, filed on Jul. 20, 2004, now abandoned, which is a continuation of application No. 09/912,139, filed on Jul. 24, 2001, now abandoned.

(30) Foreign Application Priority Data

Jul. 26, 2000    (EP) ................... 00810666

(51) Int. Cl.
C08K 5/34 (2006.01)
C08K 5/3492 (2006.01)
C08K 5/3435 (2006.01)

(52) U.S. Cl. .................. 524/99; 524/100; 524/102; 524/103

(58) Field of Classification Search .............. 524/99, 524/100, 102, 103
See application file for complete search history.

(56) References Cited

U.S. PATENT DOCUMENTS

| 4,619,956 | A | * | 10/1986 | Susi .......................... 524/87 |
| 5,288,778 | A | * | 2/1994 | Schmitter et al. ........... 524/100 |
| 5,342,862 | A | | 8/1994 | Reich ........................ 523/125 |
| 5,478,935 | A | | 12/1995 | Reinehr et al. ............. 544/180 |
| 5,591,850 | A | | 1/1997 | Birbaum et al. ............ 544/216 |
| 5,688,995 | A | | 11/1997 | Luther et al. ................ 562/30 |
| 5,736,597 | A | | 4/1998 | Birbaum et al. ............ 524/100 |
| 5,959,008 | A | | 9/1999 | Birbaum et al. ............ 524/100 |
| 5,998,116 | A | | 12/1999 | Hayoz et al. ............... 430/507 |
| 6,051,164 | A | | 4/2000 | Samuels .................... 252/404 |
| 6,060,543 | A | | 5/2000 | Bolle et al. ................. 524/100 |
| 6,239,276 | B1 | * | 5/2001 | Gupta et al. ................ 544/213 |
| 6,245,840 | B1 | | 6/2001 | Itagaki et al. ................ 524/91 |
| 6,265,473 | B1 | | 7/2001 | Galbo et al. ................ 524/100 |
| 6,348,591 | B1 | * | 2/2002 | Gupta et al. ................ 544/215 |
| 2001/0031802 | A1 | | 10/2001 | Murschall et al. ............. 524/1 |

FOREIGN PATENT DOCUMENTS

| DE | 19545896 | 6/1996 |
| DE | 19906745 | 8/1999 |
| EP | 0483488 | 5/1992 |
| EP | 0704437 | 4/1996 |
| EP | 0704560 | 4/1996 |
| EP | 0964096 | 12/1999 |
| GB | 1011575 | 12/1965 |
| GB | 2317893 | 4/1998 |
| GB | 2319523 | 5/1998 |
| GB | 2340119 | 2/2000 |
| GB | 2344596 | 6/2000 |
| JP | 8151480 | 6/1996 |
| JP | 11-322841 | 11/1999 |
| JP | 2000136270 | 5/2000 |
| JP | 2000191918 | 7/2000 |
| WO | 96/28431 | 9/1996 |
| WO | 98/06575 | 2/1998 |
| WO | 98/28966 | 7/1998 |
| WO | 99/57189 | 11/1999 |
| WO | 01/79340 | 10/2001 |

OTHER PUBLICATIONS

F. Henninger, Aspects of Greenhouse Film Stabilization, Handbook of Polymer Degradation, New York, (Month Unavailable/1992) pp. 415-416.
R. Rouveni et al., Plasticulture, vol. 102, (Feb. 1994) pp. 7-16.
Y. Antignus et al., CIPA-Congress (Mar. 1997), pp. 23-31.
Derwent Abstr. 2000-394411 [34] for JP 2000136270 (May 2000).
Derwent Abstract 96-278994/29 for DE 19545896 (Jun. 1996).
Derwent Abstract 2000-064377/06 for EP 0964096 (Dec. 1999).
Derwent Abstr. 1999-470383 for DE 19906745 (Aug. 1999).
Derwent Abstract 1996-329553 [33] for JP 8151480 (Jun. 1996).
Derwent Abstract 1999-520615 [44] for JP 11322841 (Nov. 1999).
J. Glass et al., Polyolefins 2000, The International Conference on Polyolefins, Feb. 27-Mar. 1, 2000, Houston, TX, "Effect of Pesticides on UV Stabilization", pp. 687-698.
J. Frados, Plastics Engineering Handbook of the Society of the Plastics Industry, Inc., 4th Ed., (1976), p. 273, Catalogued by the Library of Congress, (Aug. 1975).
Research Disclosure, Nov. 1997, No. 40322, "UV Stabilized Agricultural Film Products Containing Polymeric Methylated Hindered Amine Light Stabilizer Resistant to Pesticides and Fumigants", p. 768.

* cited by examiner

Primary Examiner—Kriellion Sanders
(74) Attorney, Agent, or Firm—Tyler A. Stevenson

(57) ABSTRACT

The novel transparent polyolefin, polyester or polyamide article disclosed is stabilized against the effects of light, oxygen, heat and agressive chemicals by addition of 0.005-0.30% by weight the polymeric substrate of a hydroxyphenyl triazine UV absorber, and is characterized by its thickness between 1 and 500 μm. Preferred polyolefin articles thus stabilized are agricultural films containing as further stabilizer a sterically hindered amine. The novel compositions act as selective UV filter especially useful in agriculture.

13 Claims, 4 Drawing Sheets

TRANSPARENT POLYMER ARTICLES OF LOW THICKNESS

This is a continuation of application Ser. No. 10/894,773, filed Jul. 20, 2004, abandoned, which is a continuation of application Ser. No. 09/912,139, filed Jul. 24, 2001, abandoned, the disclosures of which are incorporated by reference.

The invention relates to a novel polymer article of low thickness and good transparency having enhanced stability against the effects of light, oxygen, heat and agressive chemicals, which is also effective as a selective UV filter for agricultural applications, and to some novel stabilizers suitable for this application.

Certain polyolefin articles containing UV absorbers of the type hydroxyphenyl triazine are known from GB-A-2319523, EP-A-704437, EP-A-704560, WO 99/57189.

Present invention pertains to a transparent polyolefin, polyester or polyamide article stabilized by addition of 0.005-0.30% by weight the polymer substrate of a hydroxyphenyl triazine UV absorber, characterized in that the article has a thickness between 1 and 500 μm.

Preferred articles contain as a hydroxyphenyl triazine UV absorber a compound of the formula I

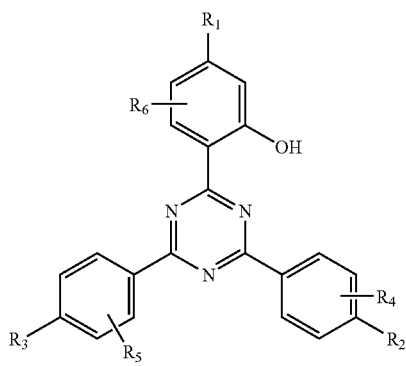

(I)

wherein $R_1$ is H or $OR_7$;

$R_2$ and $R_3$ independently are H, $C_1$-$C_8$alkyl,

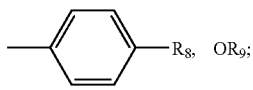

$R_4$ and $R_5$ independently are H, $C_1$-$C_8$alkyl, $OR_{10}$;

$R_6$ is H, $C_1$-$C_{18}$alkyl, $C_5$-$C_{12}$cycloalkyl, $C_7$-$C_{12}$phenylalkyl, $C_7$-$C_{12}$alkylphenyl, $C_3$-$C_{12}$alkenyl, halogen, OH, $OR_9$;

$R_8$ is H; halogen; $C_1$-$C_{12}$alkoxy; $C_1$-$C_{12}$alkyl; $C_3$-$C_{24}$alkyl interrupted by oxygen and/or substituted by OH; or is NH—CO—$R_{14}$ or NH—COO—$R_{12}$;

$R_7$, $R_9$ and $R_{10}$ independently are H; $C_1$-$C_{24}$alkyl; $C_3$-$C_{12}$alkenyl; $C_3$-$C_{24}$alkyl interrupted by oxygen and/or substituted by OH; or is $C_5$-$C_{12}$cycloalkyl, $C_7$-$C_{12}$phenylalkyl, $C_7$-$C_{12}$alkylphenyl; $CH_2CH(OH)CH_2OR_{11}$; $C_1$-$C_{12}$alkyl substituted by $COOR_{12}$, $CONR_{13}R_{14}$, $OCOR_{15}$, OH or halogen; or $R_7$ is a polymeric hydrocarbon residue of 10 to 1000 carbon atoms, preferably 20 to 500 carbon atoms;

and $R_7$ also embraces a residue of formula II

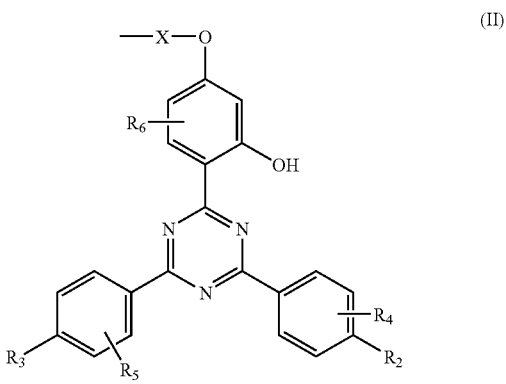

(II)

wherein X is $C_2$-$C_{24}$alkylene; —$CH_2CH(OH)CH_2$—; —$CH_2CH(OH)CH_2$O-D-O-$CH_2CH(OH)CH_2$;

($C_1$-$C_{18}$alkylene)—CO—O-D-O—CO—($C_1$-$C_{18}$alkylene); CO; CO—($C_2$-$C_{24}$alkylene)—CO; $C_3$-$C_{24}$alkylene interrupted by oxygen;

D is $C_2$-$C_{12}$alkylene; $C_4$-$C_{50}$alkylene interrupted by O; phenylene; biphenylene or phenylene-E-phenylene;

E is O, S, $SO_2$; $CH_2$; CO or —$C(CH_3)_2$—;

$R_{11}$ is H, $C_1$-$C_{12}$alkyl; phenyl; phenyl substituted by 1-3 $C_1$-$C_4$alkyl; $C_5$-$C_{12}$cycloalkyl; $C_7$-$C_{12}$phenylalkyl; $C_3$-$C_{12}$alkenyl;

$R_{12}$ is H; $C_1$-$C_{24}$alkyl; $C_3$-$C_{12}$alkenyl; $C_3$-$C_{36}$alkyl interrupted by oxygen and/or substituted by OH; or is $C_5$-$C_{12}$cycloalkyl, $C_7$-$C_{12}$phenylalkyl, $C_7$-$C_{12}$alkylphenyl; phenyl;

$R_{13}$ and $R_{14}$ independently are H, $C_1$-$C_{18}$alkyl; phenyl; phenyl substituted by 1-3 $C_1$-$C_4$alkyl and/or $C_1$-$C_4$alkoxy; $C_5$-$C_{12}$cycloalkyl; $C_3$-$C_{12}$alkenyl;

$R_{15}$ is $C_1$-$C_{12}$alkyl; phenyl; phenyl substituted by 1-3 $C_1$-$C_4$alkyl and/or $C_1$-$C_4$alkoxy; $C_5$-$C_{12}$cycloalkyl; $C_3$-$C_{12}$alkenyl; $C_1$-$C_{12}$alkoxy; or is $NR_{13}R_{14}$.

More preferably, in the hydroxyphenyl triazine UV absorber of the formula I $R_4$ and $R_5$ independently are H or methyl;

$R_6$ is H;

$R_8$ is H; $C_1$-$C_8$alkoxy; $C_1$-$C_8$alkyl;

$R_7$, $R_9$ independently are H; $C_1$-$C_{18}$alkyl; $C_3$-$C_{12}$alkenyl; $C_3$-$C_{24}$alkyl interrupted by oxygen and/or substituted by OH; or is $C_5$-$C_{12}$cycloalkyl, $C_7$-$C_{12}$phenylalkyl, $C_7$-$C_{12}$alkylphenyl; $C_1$-$C_{12}$alkyl substituted by $COOR_{12}$, $OCOR_{15}$, OH; or $R_7$ is a polymeric hydrocarbon residue of 20 to 500 carbon atoms;

and $R_7$ also embraces a residue of formula II, wherein X is $C_2$-$C_{18}$alkylene; —$CH_2CH(OH)CH_2$—; —$CH_2CH(OH)CH_2$O-D-O-$CH_2CH(OH)CH_2$;

($C_1$-$C_4$alkylene)—CO—O-D-O—CO—($C_1$-$C_4$alkylene); CO; CO—($C_2$-$C_{18}$alkylene)—CO;

$C_3$-$C_{18}$alkylene interrupted by oxygen; D is $C_2$-$C_{12}$alkylene;

$R_{12}$ is H; $C_1$-$C_{24}$alkyl; $C_3$-$C_{12}$alkenyl; $C_3$-$C_{24}$alkyl interrupted by oxygen and/or substituted by OH; or is $C_5$-$C_{12}$cycloalkyl, $C_7$-$C_{12}$phenylalkyl, $C_7$-$C_{12}$alkylphenyl; phenyl;

$R_{15}$ is $C_1$-$C_{12}$alkyl; $C_5$-$C_{12}$cycloalkyl; $C_3$-$C_{12}$alkenyl;

especially $R_1$ is $OR_7$;

$R_2$ and $R_3$ independently are H, methyl,

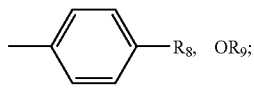

$R_4$ and $R_5$ and $R_6$ are H;

$R_8$ is H; $C_1$-$C_8$alkoxy; $C_1$-$C_4$alkyl;

$R_7$, $R_9$ independently are $C_4$-$C_{18}$alkyl or $C_5$-$C_{12}$cycloalkyl; and $R_7$ also embraces a residue of formula II, wherein X is $C_4$-$C_{18}$alkylene.

Of utmost importance are compounds of the formula I, wherein $R_1$ is $OR_7$; $R_2$ and $R_3$ each are phenyl; $R_4$, $R_5$ and $R_6$ are hydrogen; and $R_7$ is $C_4$-$C_{18}$alkyl or $C_5$-$C_{12}$cycloalkyl or a residue of formula II, wherein X is $C_4$-$C_{12}$alkylene.

A halogen substitutent is —F, —Cl, —Br or —I, preferably —F, —Cl or —Br and, in particular, —Cl.

Alkylphenyl is alkyl-substituted phenyl; $C_7$-$C_{14}$alkylphenyl embraces examples such as methylphenyl (tolyl), dimethylphenyl (xylyl), trimethylphenyl (mesityl), ethylphenyl, propylphenyl, butylphenyl, dibutylphenyl, pentylphenyl, hexylphenyl, heptylphenyl and octylphenyl.

Phenylalkyl is phenyl-substituted alkyl; $C_7$-$C_{11}$phenylalkyl embraces examples such as benzyl, α-methylbenzyl, α-ethylbenzyl, α,α-dimethylbenzyl, phenylethyl, phenylpropyl, phenylbutyl and phenylpentyl.

n-alkyl or alkyl-n is an unbranched alkyl radical.

Alkyl interrupted by O, NH, $NR_{13}$, etc., can generally comprise one or more nonadjacent heteroatoms. Preferably, a carbon atom of the alkyl chain bonds to not more than 1 heteroatom. $R_7$, $R_9$ and $R_{10}$, especially $R_7$, as alkyl substituted by $COOR_{12}$ is most preferably $CH_2$—$COOR_{12}$. $R_{12}$ is most preferably $C_1$-$C_{18}$alkyl, or $C_6$-$C_{12}$cycloalkyl; cycloalkyl is most preferably cyclohexyl or cyclododecyl.

Within the scope of the stated definitions, the radicals $R_4$, $R_5$, $R_6$, $R_8$, $R_9$, $R_{11}$, $R_{12}$, $R_{13}$, $R_{14}$, $R_{15}$ as alkyl are branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexy, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl and octadecyl.

$C_1$-$C_4$alkyl is especially methyl, ethyl, isopropyl, n-butyl, 2-butyl, 2-methylpropyl or tert-butyl.

Within the scope of the stated definitions, $R_4$, $R_5$, $R_6$, $R_8$, $R_9$, $R_{11}$, $R_{12}$, $R_{13}$, $R_{14}$, $R_{15}$ as alkenyl include allyl, isopropenyl, 2-butenyl, 3-butenyl, isobutenyl, n-penta-2,4-dienyl, 3-methyl-but-2-enyl.

$R_4$, $R_5$ and $R_6$ are most preferably hydrogen. $R_2$ and $R_3$ are most preferably phenyl or $OR_9$, especially phenyl. $R_9$ is most preferably $C_1$-$C_4$alkyl.

Examples for highly effective compounds of the formula I are as listed below or in the following tables:

2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

TABLE 1

Compounds of the formula

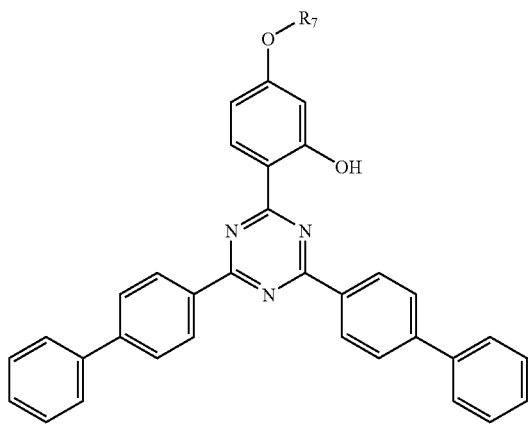

| compound | $R_7$ |
|---|---|
| a) | $CH_2CH(C_2H_5)$—$(CH_2)_3$—$CH_3$ |
| b) | $CH(CH_3)$—$(CH_2)_9$—$CH_3$ |
| c) | n-$C_6H_{13}$ |
| d) | n-$C_8H_{17}$ |
| e) | n-$C_{12}H_{25}$ |

In the above definitions, n denotes a straight alkyl chain.

TABLE 2

Compounds of the formula (k)

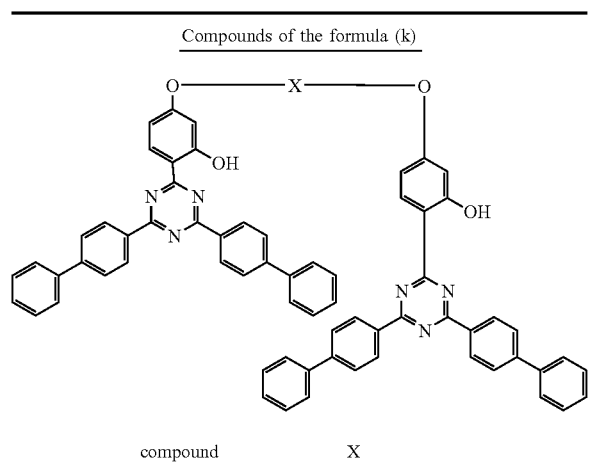

| compound | X |
|---|---|

TABLE 2-continued

| f) | —(CH$_2$)$_{12}$— |
| g) | —(CH$_2$)$_{10}$— | or corresponding compounds wherein X is $C_{13}$-$C_{24}$alkylene; ($C_1$-$C_{18}$alkylene)—CO—O-D-O—CO—($C_1$-$C_{18}$alkylene); CO—($C_{13}$-$C_{24}$alkylene)—CO; $C_3$-$C_{24}$alkylene interrupted by oxygen, especially ($C_1$-$C_3$alkylene)—O—($C_1$-$C_3$alkylene).

Further examples for highly effective compounds of the formula I are the compounds

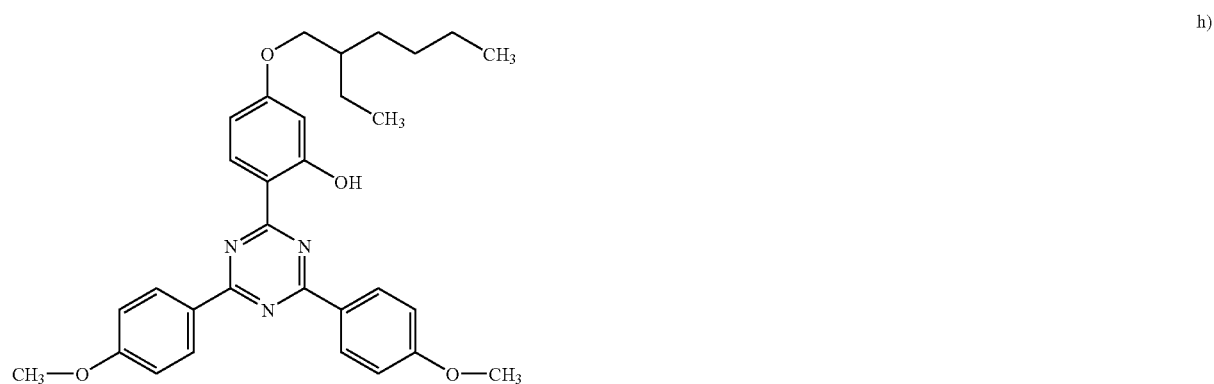

h)

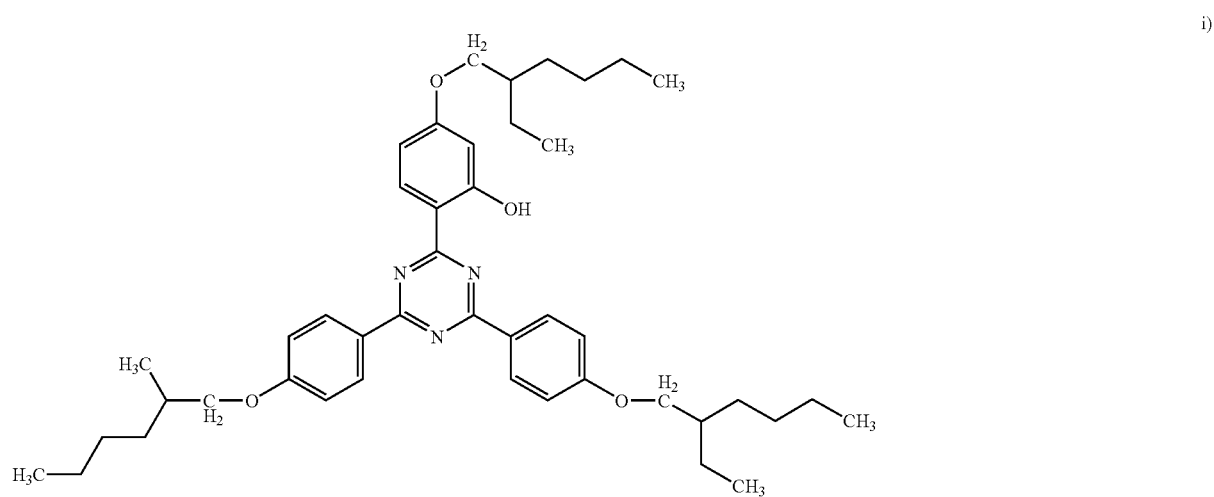

i)

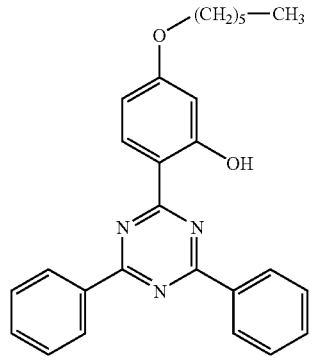

j)

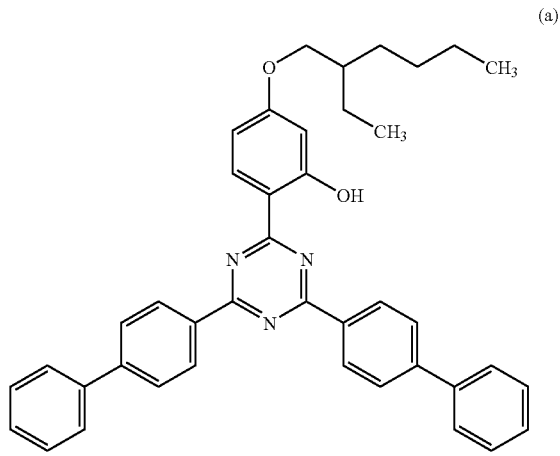

(a)

Some compounds of formula I are known, e.g. from WO 96/28431, U.S. Pat. No. 5,591,850, EP-A-434608; others, e.g. the compounds as well as (b), (f), (g) and (h) are novel compounds. They are conveniently prepared in analogy to procedures described in these references, especially to the method given in example 18 of WO 96/28431.

A particular useful application of polymer films, especially polyolefin films of present invention is their use as greenhouse films. Some types of crops are degraded by the UV-components of solar radiation which must be filtered off to obtain high quality and productivity of the crops. Additionally, some microorganisms such as fungi, e.g. *Botrytis cinerea, Botryosporium, Cladosporium cucumerium, Endomyces geotrichium, Endomyces fibulinger, Sphaerotheca pannosa, Erysiphe polygoni, Gonatobotrys, Cylindrocapron, Fusarium, Thielaviopsis, Verticillium*, and virus, e.g Cucumo-virus, Tombus-virus, etc. as well as some harmful insects, e.g. white flies, aphides, thrips or leafminers, proliferate under preferred specific UV-irradiation. These pests can be significantly reduced when UV light does not or to less extent reach the plants. [R. Reuveni et al., *Development of photoselective PE films for control of foliar pathogens in greenhouse-grown crops, Plasticulture* No. 102, p. 7 (1994); Y. Antignus et al., *The use of UV absorbing plastic sheets to protect crops against insects and spread of virus diseases, CIPA Congress* March 1997, pp. 23-33]. On the other hand, bee activity, requiring a certain band of UV radiation, needs to be retained in greenhouses in order to ensure fructification on flowering plants, e.g. tomato, cucumber, pumpkin, melon, lemon, rose, strawberry, lettuce, grape, pepper etc.

Present hydroxyphenyl triazine UV absorbers show excellent compatibility and persistence in the polyolefin, polyester or polyamide. The same time, these UV absorbers provide efficient and selective UV shielding for suppressing microbial proliferation in a protected environment, especially a plant cultivation, while retaining the UV irradiation necessary for bee, bumblebee activity. Thus, present invention also pertains to the use of a transparent polyolefin film as described above for suppressing microbial proliferation in a protected cultivation.

Examples for polyolefines to be used for manufacturing the articles of present invention include the following polymers:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Polyolefin copolymers: Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Polyesters to be used for manufacturing the articles of present invention are mainly those derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS. Preferred is polyethylene terephthalate (PET).

Polyamides are usually those derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Most preferred are polyolefines such as polyethylene, especially LDPE or LLDPE, or polypropylene.

Preferably, the amount of hydroxyphenyl triazine UV absorber in the transparent polymer article of the invention is from 0.005 to 0.15%, more preferably from 0.005 to 0.06%, especially from 0.01 to 0.06% by weight the polymer substrate.

The transparent polyolefin, polyester or polyamide article of the invention usually is a film, fiber, ribbon or stretched tape, especially an agricultural film. Its thickness preferably ranges between 1 and 300 μm, especially between 1 and 200 μm. Films, ribbons or tapes of the invention usually are not biaxially oriented. The transparent polyolefin, polyester or polyamide article of the invention often contains one or more further components, e.g. selected from further light stabilizers, processing stabilizers, fillers, clarifiers, modifiers, acid scavengers, pigments, flame retardants or other additives known in the art. These components usually do not effectively block light transmission through the present polymer articles, which is usually more than 20%, often more than 50%, and preferably more than 80% of white incoming light. For sufficient transparency, present articles preferably do not contain crystalline components in an amount that would significantly impair this property; preferably they contain no pigments and no or merely minor amounts, e.g. 0-5% by weight of the polymer, of fillers or crystalline inorganic components having lower opaquing effect than pigments (e.g. hydrotalcites). Examples for additional components which may be contained in the polymer articles of the invention include the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosohonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol-propane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, tri ethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis ($\alpha,\alpha$-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)phenyl]-benzotriazole; 2-[2'-hydroxy-3'-(1,1,3,3-tetramethylbutyl)-5'-($\alpha,\alpha$-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-p-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or with out additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethyl-piperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis (2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro-[4,5]decane, a reaction product of 7,7,9,9-tetramethyl-2-cycloundecyl-1-oxa-3,8-diaza-4-oxospiro-[4.5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-$\alpha$-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanlide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba-Geigy), tris(nonylphenyl) phosphite,

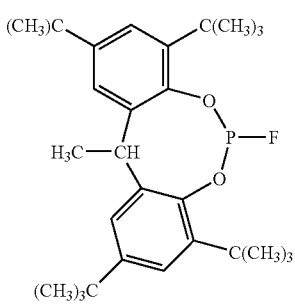

(A)

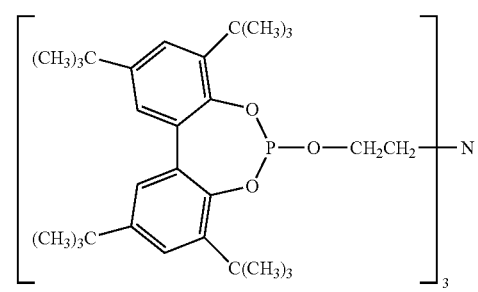

(B)

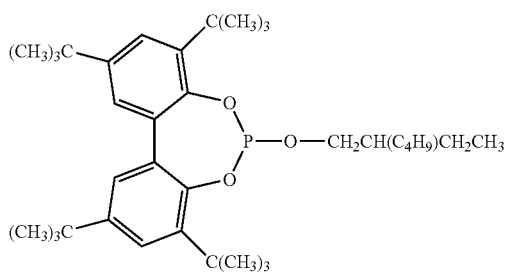

(C)

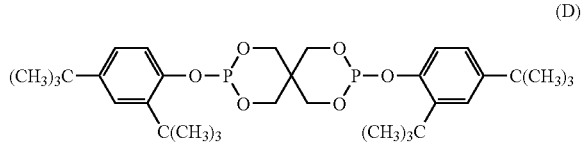

(D)

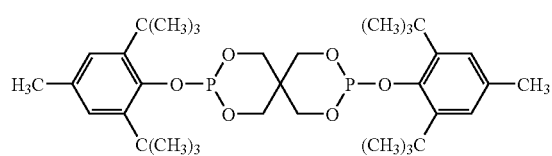

(E)

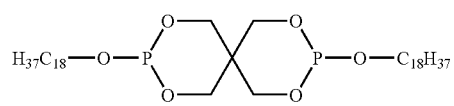

(F)

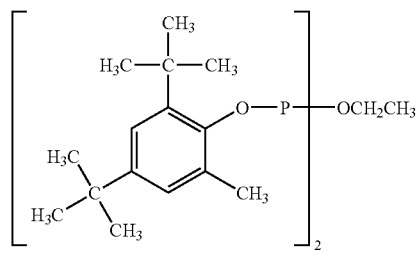

(G)

5. Hydroxalamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. 4,325,863; U.S. 4,338,244; U.S. 5,175,312; U.S. 5,216,052; U.S. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

Where appropriate, the conventional additives are judiciously employed in amounts up to 10% by weight, e.g. 0.1-10% by weight, especially 0.2-5% by weight, based on the material to be stabilized.

Acid scavengers may be added, especially in order to improve the lifetime of agricultural materials which come in contact with pesticides, e.g. greenhouse films. Components active as acid scavengers include metal oxides and/or hydroxides, e.g. oxides or hydroxides of zinc, magnesium, aluminum, calcium, mixed salts thereof, as well as hydrotalcites or zeolithes as described, for example, in GB-A-2300192, from page 2, line 2, until page 4, line 22.

Thin-walled articles of the invention, especially transparent polyolefin agricultural films, act as a selective UV filter enhancing plant growth and crop while suppressing the undesired proliferation of microorganisms. Light of the medium or far UV region (e.g. 200-360 nm, especially 300-340 nm) required by these microorganisms is effectively blocked. The same time, the activity of useful insects such as bees and bumblebees is not affected.

Preferably, the transparent polyolefin, polyester or polyamide article of the invention also contains a sterically hindered amine as further stabilizer in order to obtain optimum light stability of the substrate. The sterically hindered amine is usually contained in an amount of 0.01-6% by weight the polyolefin, polyester or polyamide, the weight ratio sterically hindered amine:hydroxyphenyl triazine UV absorber preferably ranging from 2:1 to 20:1.

Examples for sterically hindered amines preferably contained in the polyolefin, polyester or polyamide articles of the invention are given in the above list (item 2.6).

More preferred sterically hindered amines include the following compounds: bis(2,2,6,6-tetramethyl-4-piperidyl) sebacate; bis(1,2,2,6,6-pentamethyl-4-piperidyl)sebacate; the condensate of 1-(2-hydroxyethyl)-2,2,6,6-tetramethyl-4-hydroxypiperidine and succinic acid (CAS-No. 65447-77-0); N,N',N",N'''-Tetrakis(4,6-bis(butyl-(N-methyl-2,2,6,6-tetramethylpiperidin-4-yl)amino)triazin-2-yl)-4,7-diazadecane-1,10-diamine (CAS-No. 106990-43-6);

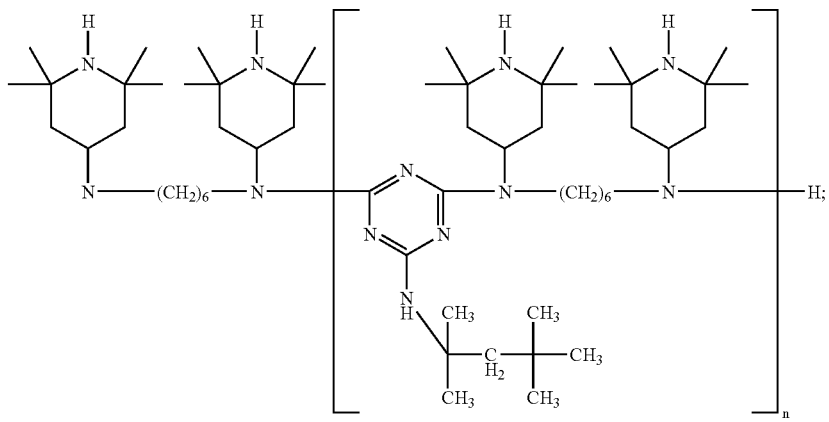

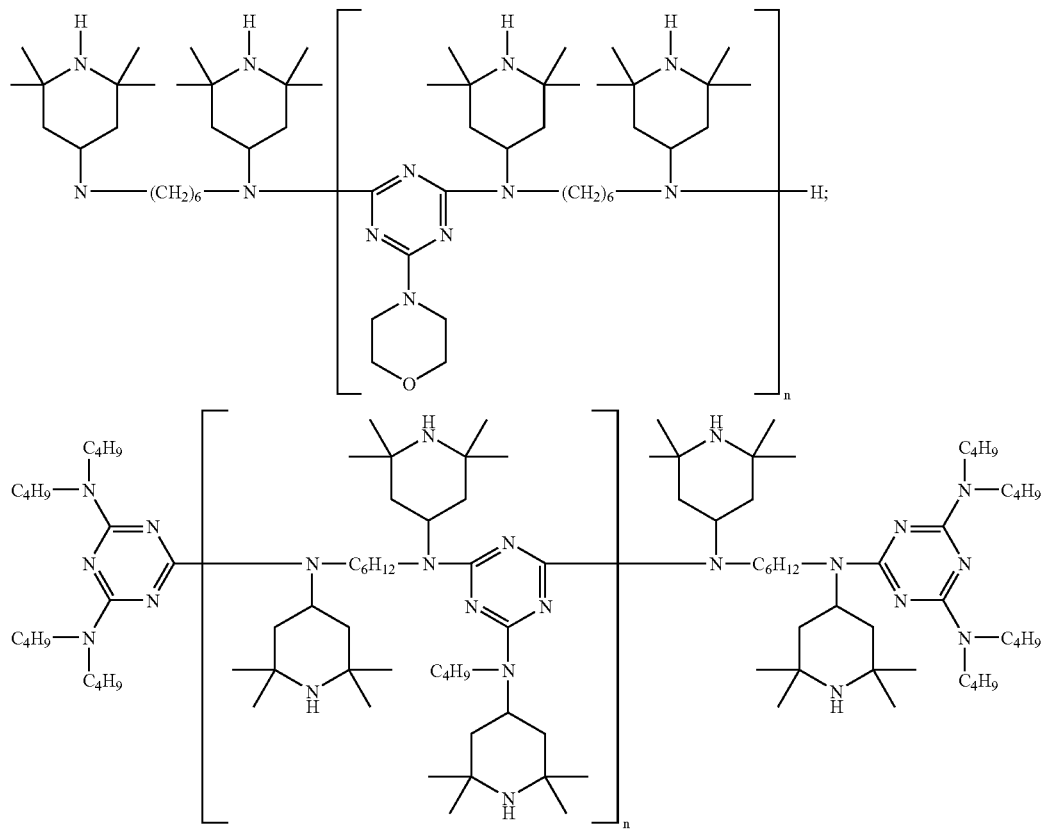

(Chimassorb® 2020, CAS No. 192268-64-7), where n is mainly from the range 3-5; or mixtures of these compounds.

Best results are obtained with a sterically hindered amine from the class of the hydroxylamine ethers. Sterically hindered hydroxylamine ethers are mainly piperidine derivatives containing one or more functional groups of the formula

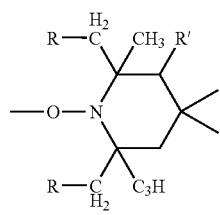

wherein R and R' independently are hydrogen or methyl, and at least the chemical bond of the oxygen atom and optionally a further chemical bond is linked to an organic residue while the remaining is/are saturated with hydrogen; or all 3 chemical bonds are linked to an organic residue. Examples for such compounds are described inter alia in U.S. Pat. Nos. 5,204,473, 5,216,156, or in GB-A-2347928.

Examples for the most preferred hydroxylamine ethers are compounds of the formula (1g-1)

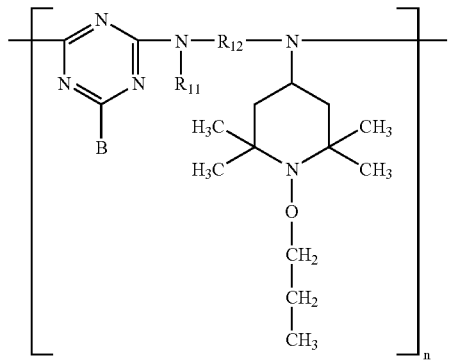

in which the index n ranges from 1 to 15, being especially from the range 3-9;

$R_{12}$ is $C_2$-$C_{12}$alkylene, $C_4$-$C_{12}$alkenylene, $C_5$-$C_7$cycloalkylene, $C_5$-$C_7$cycloalkylene-di($C_1$-$C_4$alkylene), $C_1$-$C_4$alkylenedi($C_5$-$C_7$cycloalkylene), phenylenedi($C_1$-$C_4$alkylene) or $C_4$-$C_{12}$alkylene interrupted by 1,4-piperazinediyl, —O— or >N—$X_1$ with $X_1$ being $C_1$-$C_{12}$acyl or ($C_1$-$C_{12}$alkoxy)carbonyl or having one of the definitions of $R_{14}$ given below except hydrogen;

or $R_{12}$ is a group of the formula (Ib') or (Ic');

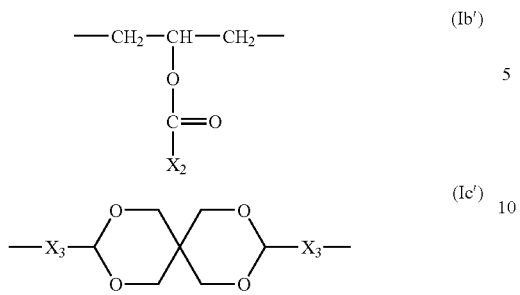 (Ib')

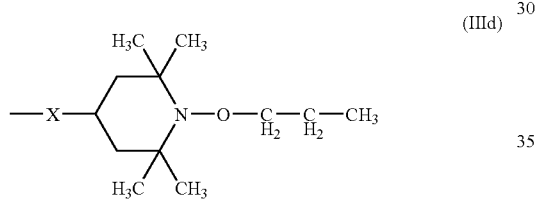 (Ic')

with m being 2 or 3,

X$_2$ being C$_1$-C$_{18}$alkyl, C$_5$-C$_{12}$cycloalkyl which is unsubstituted or substituted by 1, 2 or 3 C$_1$-C$_4$alkyl; phenyl which is unsubstituted or substituted by 1, 2 or 3 C$_1$-C$_4$alkyl or C$_1$-C$_4$alkoxy; C$_7$-C$_9$phenylalkyl which is unsubstituted or substituted on the phenyl by 1, 2 or 3 C$_1$-C$_4$alkyl; and the radicals X$_3$ being independently of one another C$_2$-C$_{12}$alkylene; the radicals B are independently of one another Cl, —OR$_{13}$, —N(R$_{14}$)(R$_{15}$) or a group of the formula (IIId);

 (IIId)

R$_{13}$, R$_{14}$ and R$_{15}$, which are identical or different, are hydrogen, C$_1$-C$_{18}$alkyl, C$_5$-C$_{12}$cycloalkyl which is unsubstituted or substituted by 1, 2 or 3 C$_1$-C$_4$alkyl; C$_3$-C$_{18}$alkenyl, phenyl which is unsubstituted or substituted by 1, 2 or 3 C$_1$-C$_4$alkyl or C$_1$-C$_4$alkoxy; C$_7$-C$_9$phenylalkyl which is unsubstituted or substituted on the phenyl by 1, 2 or 3 C$_1$-C$_4$alkyl; tetrahydrofurfuryl or C$_2$-C$_4$alkyl which is substituted in the 2, 3 or 4 position by —OH, C$_1$-C$_8$alkoxy, di(C$_1$-C$_4$alkyl)amino or a group of the formula (Ie');

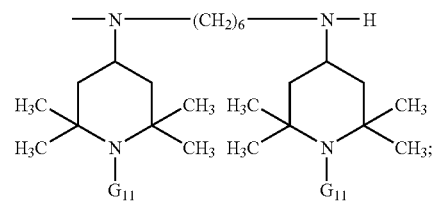 (Ie')

with Y being —O—, —CH$_2$—, —CH$_2$CH$_2$— or >N—CH$_3$, or —N(R$_{14}$)(R$_{15}$) is additionally a group of the formula (Ie');

X is —O— or >N—R$_{16}$;

R$_{16}$ is hydrogen, C$_1$-C$_{18}$alkyl, C$_3$-C$_{18}$alkenyl, C$_5$-C$_{12}$cycloalkyl which is unsubstituted or substituted by 1, 2 or 3 C$_1$-C$_4$alkyl; C$_7$-C$_9$phenylalkyl which is unsubstituted or substituted on the phenyl by 1, 2 or 3 C$_1$-C$_4$alkyl; tetrahydrofurfuryl, a group of the formula (IIIf),

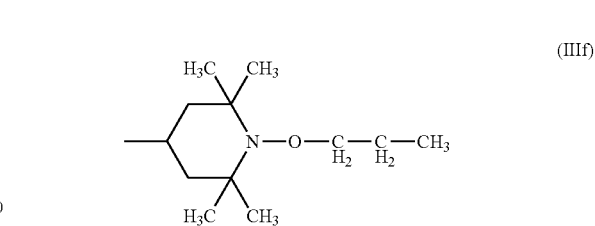 (IIIf)

or C$_2$-C$_4$alkyl which is substituted in the 2, 3 or 4 position by —OH, C$_1$-C$_8$alkoxy, di(C$_1$-C$_4$alkyl)amino or a group of the formula (Ie');

R$_{11}$, has one of the definitions given for R$_{16}$.

In these compounds, the end group bonded to the triazine residue can be, for example, a group B or —N(R$_{11}$)—R$_{12}$—B, such as chlorine or a group

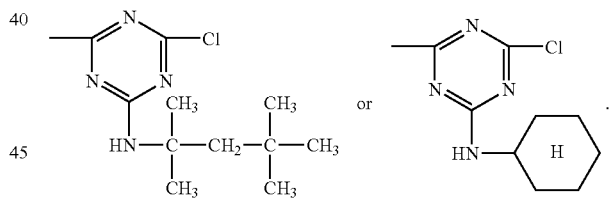

and the end group bonded to the diamino group can be, for example, hydrogen or a di-B-substituted triazinyl group, such as a group

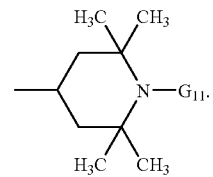

It may be convenient to replace the chlorine attached to the triazine by e.g. —OH or an amino group. Suitable amino groups are typically: pyrrolidin-1-yl, morpholino, —NH$_2$, —N(C$_1$-C$_8$alkyl)$_2$ and —NY'(C$_1$-C$_8$alkyl) wherein Y' is hydrogen or a group of the formula In the above shown oligomeric and polymeric compounds, examples of alkyl are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl and docosyl;

examples of cycloalkyl are cyclopentyl, cyclohexyl, cycloheptyl and cyclooctyl;

an example of $C_7$-$C_9$phenylalkyl is benzyl; and examples of alkylene are ethylene, propylene, trimethylene, tetramethylene, pentamethylene, 2,2-dimethyltrimethylene, hexamethylene, trimethylhexamethylene, octamethylene and decamethylene.

Another example for a sterically hindered amine ether advantageously to be used within present polymer articles is the compound of the formula

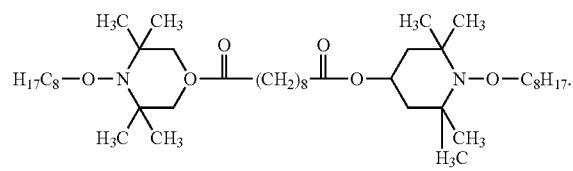

An example for a highly effective compound of formula (1g-1) is the compound of the formula (1g-2)

or mixed with one another. If desired, the individual components can be mixed with one another for example in the melt (melt blending) before incorporation into the polymer.

The incorporation of the additives of the invention and optional further components into the polymer is carried out by known methods such as dry mixing in the form of a powder, or wet mixing in the form of solutions or suspensions. The additives of the invention and optional further additives may be incorporated, for example, before or after molding or also by applying the dissolved or dispersed additive or additive mixture to the polymer material, with or without subsequent evaporation of the solvent. They may be added direct into the processing apparatus (e.g. extruders, internal mixers, etc), e.g. as a dry mixture or powder or as solution or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The additives of the invention and optional further additives can also be added to the polymer in the form of a masterbatch which contains the components in a concentration of, for example, about 2.5% to about 25% by weight; in such operations, the polymer can be used in the form of powder, granules, solutions, suspensions or in the form of latices.

The examples which follow describe the invention further without constituting any restriction. Parts and percentages therein are by weight; an example which mentions room temperature means thereby a temperature in the range 20-25° C. In the case of solvent mixtures such as those for

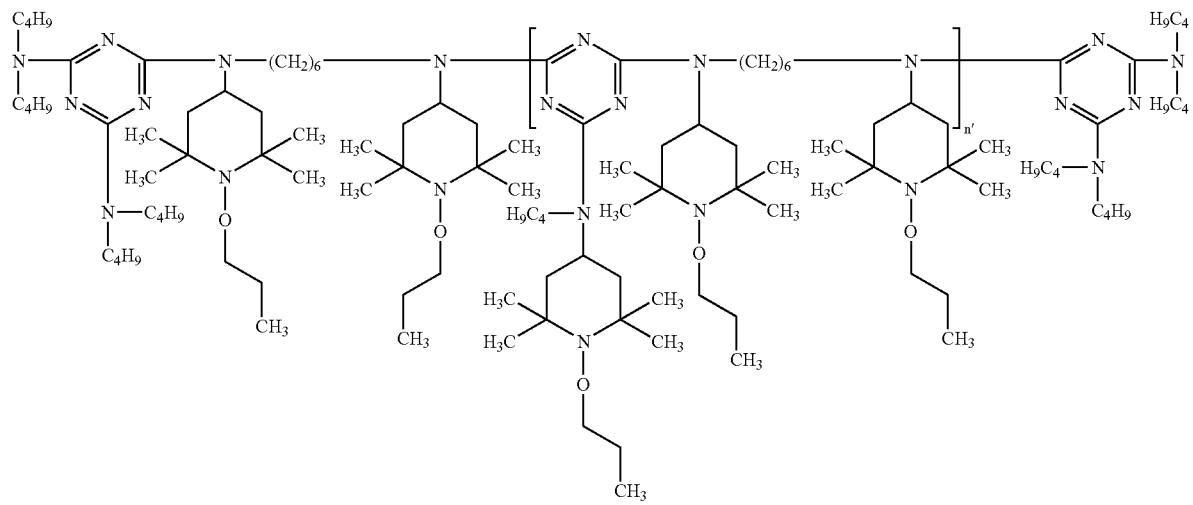

wherein n' is approximately 3 (example 2 of GB-A-2334717, CAS # 247243-62-5, which is the NO-n-propyl derivative of the block oligomer Chimassorb® 2020 CAS # 192268-64-7, Ciba Specialty Chemicals Corp.).

The additives of the invention and optional further components may be added to the polymer material individually chromatography the parts indicated are by volume. These definitions apply unless specified otherwise.

The following abbreviations are used:

m.p. melting point or melting range

NMR nuclear magnetic resonance $T_g$ glass transition temperature;

h: hours.

Preparation of Hydroxyphenyl Triazine UV Absorbers

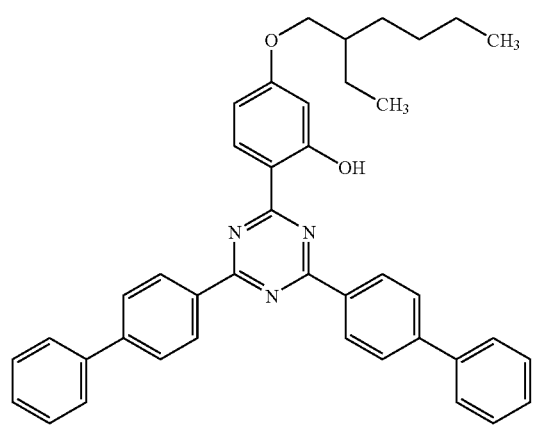

a)

Synthesis of 2,4-bis-biphenyl-6-[2-hydroxy-4-(2-ethyl-hexyloxy)phenyl]-1,3,5-triazine A yellow suspension of 2,4-bis-biphenyl-6-[2,4-dihydroxyphenyl]-1,3,5-triazine (11.2 g, 0.0227 mole) in dimethylformamide (30 ml) is heated under nitrogen at 70° until a clear brown solution is formed. Anhydrous potassium carbonate (3.77 g, 0.0227 mole) is added and the brown suspension heated at 80° C. for 30 minutes. 2-Ethylhexylbromide (5.70 g, 0.0295 mole) is added dropwise over 30 minutes, after which the suspension is heated at 110° C. for a further 3 hours. Precipitated salts are filtered off and the filtrate cooled to 0° C. Methanol (20 ml) is added and the precipitated product removed by filtration. After drying under vacuum, 2,4-bis-biphenyl-6-[2-hydroxy-4-(2-ethylhexyloxy-phenyl]-1,3,5-triazine (12.8 g) is obtained with mp 70°.

h) When in the above preparation the educt 2,4-bis-biphenyl-6-[2,4-dihydroxyphenyl]-1,3,5-triazine is replaced by the equivalent amount of 2,4-bis(4-methoxyphenyl)-6-[2,4-dihydroxyphenyl]-1,3,5-triazine, compound (h) of the formula

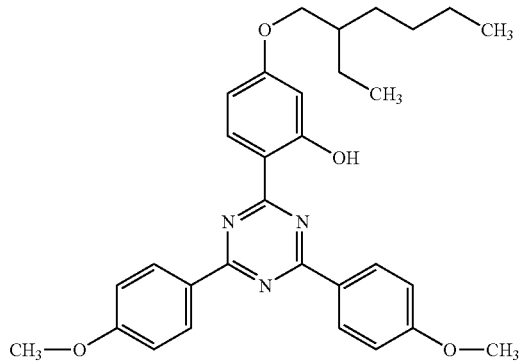

is obtained with mp 105° C.,

The compounds shown in the following table are obtained when the above reaction (a) is repeated using corresponding amounts of other alkylbromides or alkylene-dibromides.

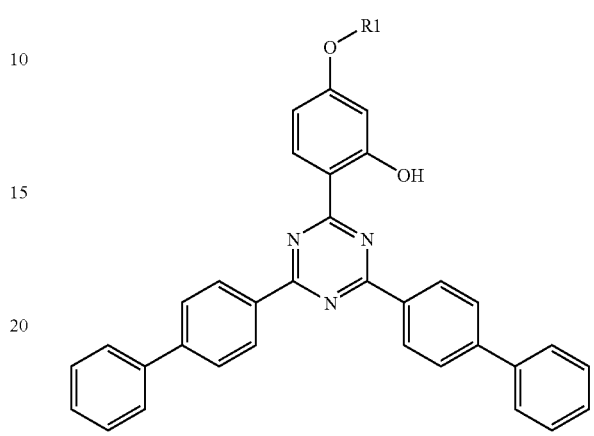

| Example | R-1 | Mp: ° C. |
|---------|-----|----------|
| b) | $CH(CH_3)—(CH_2)_9—CH_3$ | OIL |
| c) | $n-C_6H_{13}$ | 178 |
| d) | $n-C_8H_{17}$ | 160 |
| e) | $n-C_{12}H_{25}$ | 146 |

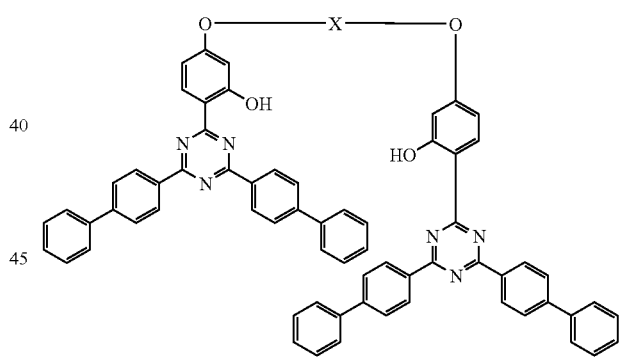

| Example | X | Mp: ° C. |
|---------|---|----------|
| f) | $—(CH_2)_{10}—$ | >250 |
| g) | $—(CH_2)_{12}—$ | >250 |

Corresponding compounds wherein X is $C_{13}$-$C_{24}$alkylene; ($C_1$-$C_{18}$alkylene)—CO—O-D-O—CO—($C_1$-$C_{18}$alkylene); CO—($C_{13}$-$C_{24}$alkylene)—CO; $C_3$-$C_{24}$alkylene interrupted by oxygen, especially ($C_1$-$C_3$alkylene)—O—($C_1$-$C_3$alkylene) are obtained using the appropriate alkylene-dibromides or alkylene-dibromides interrupted by —CO—O-D-O—CO— or oxygen, or dichlorides or dibromides of aliphatic $C_{15}$-$C_{26}$diacids.

l) Preparation of the compound of the formula:

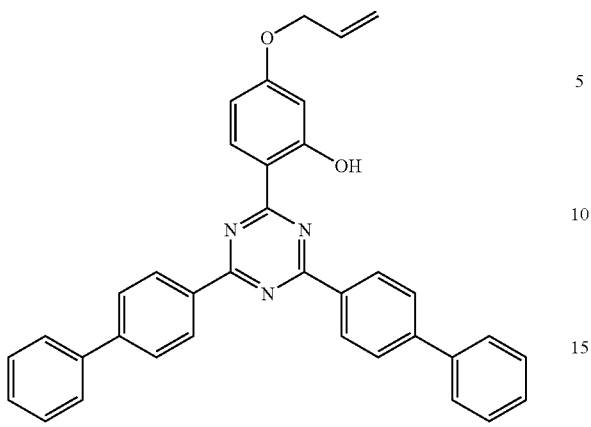

In a manner analogous to Example 16 of WO 96/28431, a white powder is obtained from the starting material: 4-(4,6-bis-biphenyl-4-yl-(1,3,5)triazin-2-yl)-benzene-1,3-diol and allyl bromide.

$^1$H NMR (300 MHz, CDCl$_3$): δ=13.3 (s, 1H), 8.7-6.2 (aromatic signals, 21H), 6.1 (m, 1H), 5.3 (m, 2H), 4.3 (m, 2H).

m) Preparation of the oligomer of the formula:

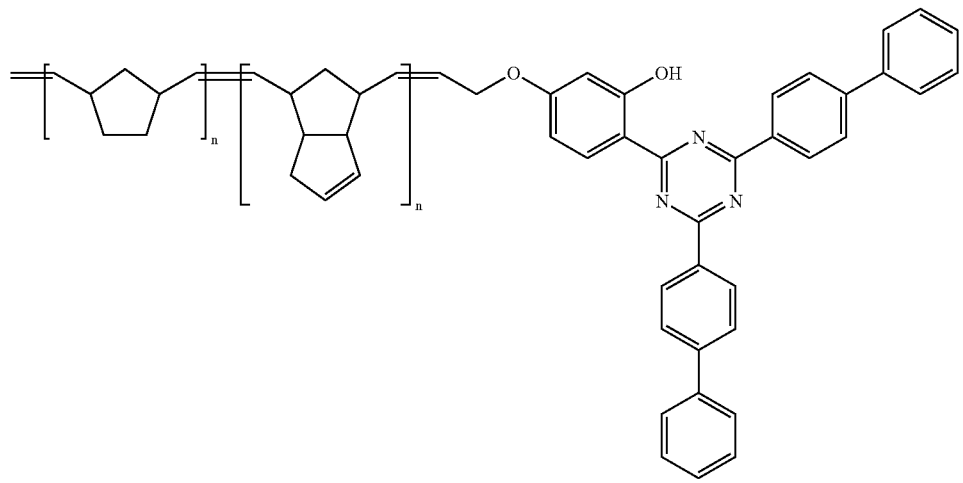

30 g (0.056 mol) of the compound from Example (I) and 30.2 g (0.320 mol) of norbornylene and 42.3 g (0.320 mol) of dicyclopentadiene and 0.49 g (0.6 mmol) of the catalyst bis(tricyclopentylphosphine)dichloro(3-methyl-2-butenylidene)ruthenium (APT Cat ASMC 716) are added to 300 ml of toluene. The mixture is left to react for 24 hours at 300. The solution is then concentrated under vacuum and a pale brown solid is obtained.

Visual melting range: 168-180° C.; M$_n$: 2216; M$_w$: 4663; PDI: 2.10;

Elemental analysis:

|  | % C | % H | % N |
| --- | --- | --- | --- |
| theory | 87.5 | 8.4 | 2.3 |
| found | 85.8 | 8.6 | 2.1 | n) Preparation of the hydrogenated oligomer of the formula:

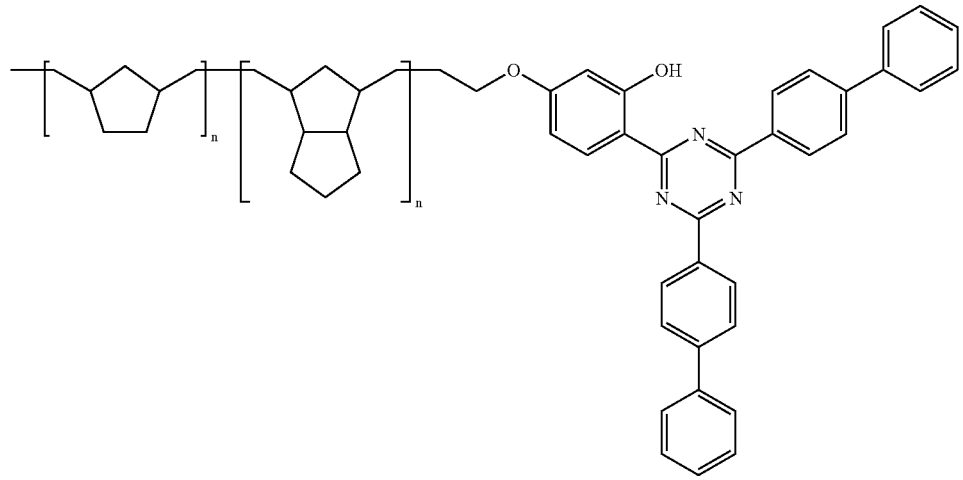

To a solution of 92 g (0.050 mol) of the oligomer of Example (m) in 300 ml of xylene, 1.0 g of platinum on carbon (10% w/w) is added. The mixture is poured into an autoclave and hydrogenated for 24 hours at 65 bar ($p_{H2}$) and 105° C. The hydrogenated mixture is purified from the catalyst by adding 10 g of Tonsyll© 414 FF at 80-90° C. and left under vigorous stirring for 2 hours. After filtering off over a pad of 10 g of Tonsil the filtrated yellow solution is concentrated under vacuum and a pale yellow solid is obtained.

Visual melting range: 55-68° C.; $M_n$: 2197; $M_w$: 4347; PDI: 1.98;

$\epsilon$ (290 nm, toluene): 34574;

Elemental analysis:

|  | % C | % H | % N |
|---|---|---|---|
| theory | 85.8 | 10.2 | 2.2 |
| found | 84.7 | 10.2 | 2.0 |

APPLICATION EXAMPLES

In some of the application examples, the following sterically hindered amines (HALS) are employed:

| compound | formula/chemical name |
|---|---|
| (1g-2) | [structure shown] |
| H-2 | bis(2,2,6,6-tetramethyl-4-piperidyl)sebacate) |
| H-3 | condensate of 1-(2-hydroxyethyl)-2,2,6,6-tetramethyl-4-hydroxypiperidine and succinic acid (CAS-No. 65447-77-0) |

| compound | formula/chemical name |
|---|---|
| H-4 | 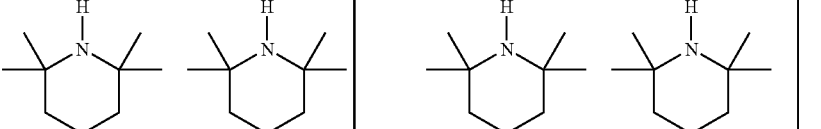 |
| H-5 | N,N',N'',N'''-Tetrakis(4,6-bis(butyl-(N-methyl-2,2,6,6-tetramethylpiperidin-4-yl)amino)triazin-2-yl)-4,7-diazadecane-1,10-diamine (CAS-No. 106990-43-6). |

Example 1

Combination Hydroxyphenyl Triazine Compound (a) with Compound (1g-2)

In order to evaluate the UV-absorber characteristics of hydroxyphenyl triazine compound (a), when mixed with a commercial thermoplastic material, thin low density polyethylene (LDPE) films are prepared, containing, as a typical formulation, 0.15% by weight of the above compound (a) and 0.70% of the sterically hindered amine ether (1g-2), used as light stabilizer of the polymeric system in highly demanding environments for agriculture applications. To do so, properly weighted amounts of the compounds are mixed with ground LDPE (Polimeri Europa, supplied by Enichem, Milano, Italy), characterized by a density of 0.921 g/cm³ and a melt flow index (190° C./2.16 kg) of 0.6 in a turbo mixer. The mixture is extruded at a maximum temperature of 200° C. in a OMC® twin-screw extruder. The granules so obtained are blown in a lab scale Formac® blow-extruder at a maximum temperature of 210° C. to give a film of 150 μm thickness.

UV-Vis spectrum of the film as-obtained is recorded in the range 200-800 nm by means of a Perkin-Elmer lambdas® 20 spectrophotometer, equipped with a RSA-PE-20 Labsphere® integrating sphere. At 0.15% loading, compound (a) imparts to the film a strong UV absorption feature, with a transmittance value less than 10% between 290 and 360 nm and less than 1% between 300 and 340 nm. The photostability of compound (a) is demonstrated by exposing the film sample to UV light in an Atlas Ci 65 Xenon Arc Weather-O-meter® (WOM, 63° C. black panel temperature, continuos dry cycle, according to ASTM G 26-96). After 1500 hours of WOM exposure the minimum transmittance displayed by the film is still around 1% at 320 nm.

Compound (a) is fully compatible in LDPE film; no blooming is observed after storage of the film for 6000 hours at room temperature. Same behavior is observed keeping the film for the same amount of time in oven at 60° C. After the same time of exposure in oven, no significant change in the UV-Vis absorption spectrum is observed, meaning there is no loss of additive, because of the high temperature.

WOM exposure of the formulation reported in this example is continuing, in order to evaluate the light stability performance of the polymer containing compound (a). Samples are also being exposed to natural weathering and are subdued to treatments with pesticides, in order to evaluate the resistance to chemicals that can be employed in agriculture.

Example 2

Hydroxyphenyl Triazine Compound (c) as a UV Filter in a Polyethylene Agrofilm In order to prepare thin LDPE films and to evaluate the spectral features imparted by the additive and its persistency, compound (c) is mixed with LDPE pellets (Riblene FF 29, supplied by Polimeri Europa, Milano, Italy), characterized by a density of 0.921 g/cm³ and a melt flow index (190° C./2.16 Kg) of 0.6) in a turbo mixer in order to give a formulation containing 0.15% by weight of the additive. The mixture is extruded at a maximum temperature of 200° C. in a OMC twin-screw extruder. The granules so obtained are blown in a lab scale Formac blow-extruder at a maximum temperature of 210° C. to give a film 150 μm thick. UV-Vis spectra are recorded in the range 200-800 nm by means of a Perkin-Elmer Lambda 20 spectrophotometer, equipped with a RSA-PE-20 Labsphere integrating sphere.

Results: The film displays a strong absorption band in the range 280-360 nm. In particular, transmittance is below 20% in the above mentioned range and below 5% in the range 295-345 nm.

In order to test the photostability of the additive upon exposure to light, a portion of the film is exposed in an Atlas Weather-o-Meter (WOM), model Ci65A (as per ASTM G26-96, irradiance 0.35 W/m², black panel temperature 63±3° C.). After 1000 hours of exposure the film still displays a transmittance below 40% between 280 and 360 nm and below 25% between 295 and 345 nm.

Example 3

A film containing 0.15% by weight of compound (d) is prepared as described in example 2. The film displays a strong absorption band in the range 280-360 nm. In particular, transmittance is below 20% in the above mentioned range and below 5% in the range 295-345 nm.

After 1000 hours of exposure in the WOM (see example 2 for details), the film still retains the spectral features described above.

Another portion of the film is also exposed in a forced circulating air oven at 60° C., in order to evaluate the thermal persistency of the additive in the film. After 1000 hours of exposure the film still retains the initial spectral features.

Example 4

A film containing 0.15% by weight of compound (b) is prepared as described in example 2. The film displays a strong absorption band in the range 280-360 nm. In particular, transmittance is below 20% in the above mentioned range and below 5% in the range 295-345 nm.

After 1000 hours of exposure in the WOM (see example 2 for details), the film still retains the spectral features described above.

Example 5

A film containing 0.15% by weight of compound (g) is prepared as described in example 2. The film displays a strong absorption band in the range 280-360 nm. In particular, transmittance is below 20% in the above mentioned range and below 5% in the range 295-345 nm.

After 1000 hours of exposure in the WOM (see example 2 for details), the film still displays a transmittance below 25% between 280 and 360 nm and below 10% between 295 and 345 nm.

Another portion of the film is also exposed in oven at 60° C. After 1000 hours of exposure the film retains about 75% of the initial absorption.

Example 6

A film containing 0.15% by weight of compound (f) is prepared as described in example 2. The film displays a strong absorption band in the range 280-360 nm. In particular, transmittance is below 20% in the above mentioned range and below 5% in the range 295-345 nm.

After 1000 hours of exposure in the WOM (see example 2 for details), the film still displays a transmittance below 25% between 280 and 360 nm and below 15% between 295 and 345 nm.

Example 7

Light Stabilization of Polypropylene (PP) Cast Films 100 parts of polypropylene powder (melt flow index 3.8 g/10 minutes, 230° C./2160 g) are blended in a barrel mixer with 0.05 parts of pentaerythrityl-tetrakis-3-(3,5-di-tert.butyl-4-hydroxyphenyl)-propionate, 0.05 parts of tris-(2,4-di-tert.butylphenyl)-phosphite, 0.1 parts of Ca stearate, 0.1 part HALS and the amount of UV absorber (compound j) indicated in the figures below. Then the blend is compounded in an extruder at temperatures of 180-220° C. The granules obtained on extrusion and granulation are transformed into films at 220-260° C. in a second extruder equipped with a flat sheet die. Samples of 60×25 mm are cut out of these 0.11 mm films and exposed in a WEATHER-OMETER Ci 65 (black panel temperature 63±2° C., without water-spraying).

Periodically, these samples are removed from the exposure apparatus and their carbonyl content is measured with an infrared spectrophotometer. The exposure time corresponding to formation of a carbonyl absorbance of 0.1 is a measure for the stabilizing efficiency of the light stabilizer. The values obtained are plotted in FIGS. 1, 2 and 3. The following HALS are used (0.1 part of each per 100 parts PP):

FIG. 1: Low molecular mass HALS H-2 (bis(2,2,6,6-tetramethyl-4-piperidyl)sebacate);

FIG. 2: Polymeric HALS H-3 (CAS-No. 65447-77-0, white circles); polymeric HALS H-4 (white squares); and blend of 1 part H-3 with 1 part H-4 (filled circles);

FIG. 3: non-polymeric high molecular mass HALS H-5.

The plots show that already small amounts of the hydroxyphenyl triazine UV absorber give considerable improvement of the UV stability conferred by HALS.

Example 8

Light stabilization of polypropylene tapes 100 parts of polypropylene powder (melt flow index 3.5 g/10 minutes, 230° C./2160 g) are blended in a barrel mixer with 0.05 parts of pentaerythrityl-tetrakis-3-(3,5-ditert.butyl-4-hydroxyphenyl)-propionate, 0.05 parts of tris-(2,4-di-tert.butylphenyl)-phosphite, 0.1 parts of Ca stearate, 0.1% polymeric HALS H-3 (condensate of 1-(2-hydroxyethyl)-2,2,6,6-tetramethyl-4-hydroxypiperidine and succinic acid (CAS-No. 65447-77-0)) and the amount of light stabilizer compound (j) indicated in the figure. Then the blend is compounded in an extruder at temperatures of 180-220° C. The granules obtained on extrusion and granulation are transformed into films at 220-260° C. in a second extruder equipped with a flat sheet die. The films are cut into ribbons, which are drawn to achieve a stretch ratio of 1:6. The tapes obtained with this procedure are finally 50 µm thick and 2.5 mm wide.

The tapes are mounted without tension on sample holders and subjected to natural weathering in Florida (45° South, direct, approximately 140 kLy/year). Periodically, the tensile strength of the exposed tapes is measured. The received energy (in kLy) corresponding to a loss of 50% of the initial tensile strength is a measure for the stabilizing efficiency of the light stabilizer. The values obtained with a polymeric HALS and the hydroxyphenyl triazine UV absorber are plotted in FIG. 4.

The results show that the contribution of the UV absorber to light stability is also marked in PP tapes that are less than half as thick as the PP films used in Example 7.

Example 9

Light Stabilization of Polypropylene Tapes 100 parts of polypropylene powder (melt flow index 3.5 g/10 minutes, 230° C./2160 g) are blended in a barrel mixer with 0.05 parts of pentaerythrityl-tetrakis-3-(3,5-ditert.butyl-4hydroxyphenyl)-propionate, 0.05 parts of tris-(2,4-di-tert.butyl-phenyl) phosphite, 0.1 parts of Ca stearate and the amount of light stabilizers indicated in the below table. Then the blend is compounded in an extruder at temperatures of 180-220° C. The granules obtained on extrusion and granulation are transformed into films at 220-260° C. in a second extruder equipped with a flat sheet die. The films are cut into ribbons, which are drawn to achieve a stretch ratio of 1:6. The tapes obtained with this procedure are finally 50 µm thick and 2.5 mm wide.

The tapes are mounted without tension on sample holders and exposed in a WEATHER-O-METER Ci 65 (black panel temperature 63±2° C., without water-spraying). Periodically, the tensile strength of the exposed tapes is measured. The exposure time corresponding to a loss of 50% of the initial tensile strength (T50) is a measure for the stabilizing efficiency of the light stabilizer.

The values obtained are summarized in the below table.

TABLE

Effect of various UV absorber types on the performance of HALS in PP tapes.

| HALS | UV Absorber | T50 (h) |
|---|---|---|
| none | none | 530 |
| 0.1% H-3 | none | 2150 |
| 0.1% H-3 | 0.1% V-1 | 2500 |
| 0.1% H-3 | 0.1% V-2 | 2700 |
| 0.1% H-3 | 0.1% compound j | 3800 |
| 0.1% H-4 | none | 3000 |
| 0.1% H-4 | 0.1% V-2 | 2900 |
| 0.1% H-4 | 0.1% compound j | 4150 |

Compound V-1 is 2-(2'-hydroxy-3'-t-butyl-5'-methylphenyl)-5-chlorobenzotriazole.
Compound V-2 is of the formula

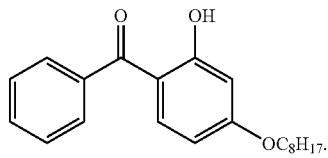

The data show that the contribution of the hydroxyphenyl triazine UV absorber (compound j) to the light stability of the tapes is significant while the contribution of the benzotriazole or the benzophenone UV absorber (V-1 and V-2) remains small or not detectable.

Example 10

Absorption Band and Persistency in LDPE of Compound (m)

Thin low density polyethylene (LDPE) films are prepared as described in example 2 but without addition of HALS. They are 150 μm thick and contain 0.5% of the compound (m). UV-Vis spectra are recorded as described in example 2. The film displays a strong absorption in the range 280-360 nm. Transmittance values below 3% are detected in the range 290-350 nm.

The persistency of the polymer in LDPE films is determined after exposure of the films at 60° C. in a forced circulating air oven and evaluated as described in example 3. No decrease of the absorbance value at the maximum is observed after 3000 hours at 60° C.

Figure 1:
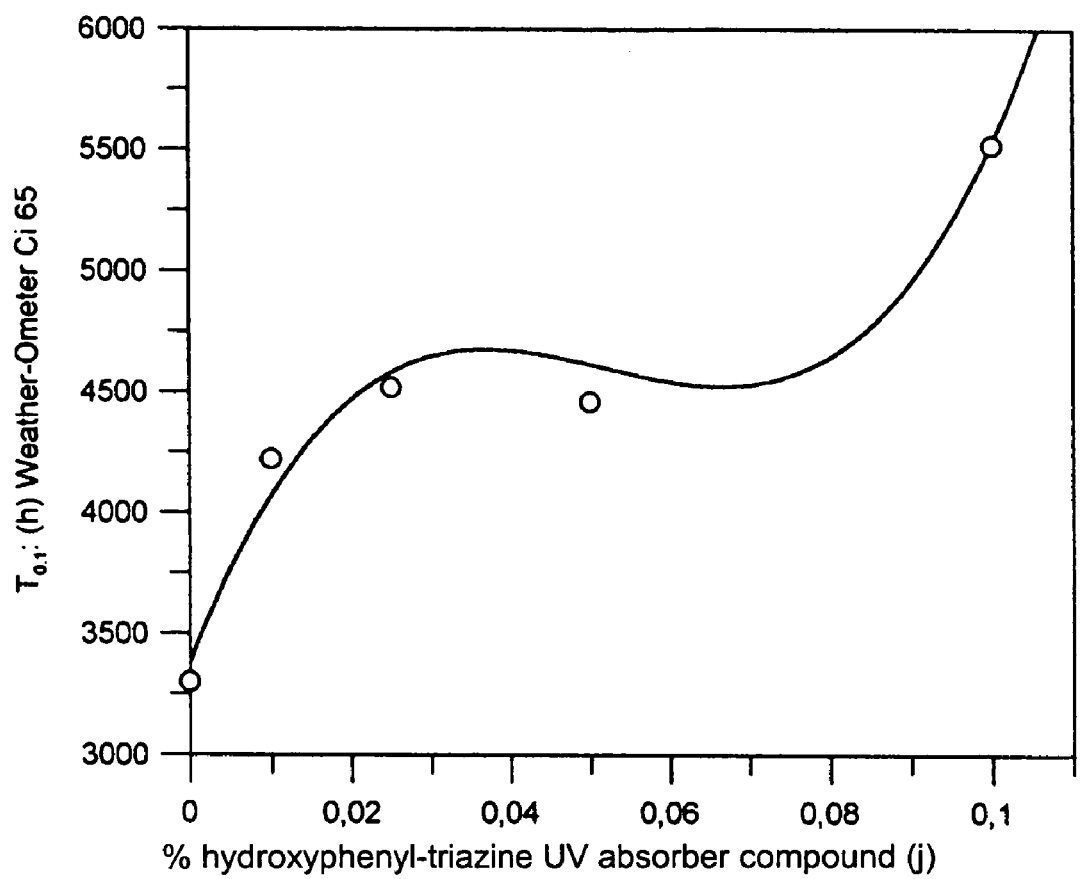
FIG. 1: Effect of the addition of hydroxyphenyl-triazine UV absorber compound (j) in presence of a low molecular mass HALS H-2 in PP cast films (0.1 mm thick). $T_{0.1}$=exposure time to 0.1 carbonyl absorbance. Example 7.
Figure 2:
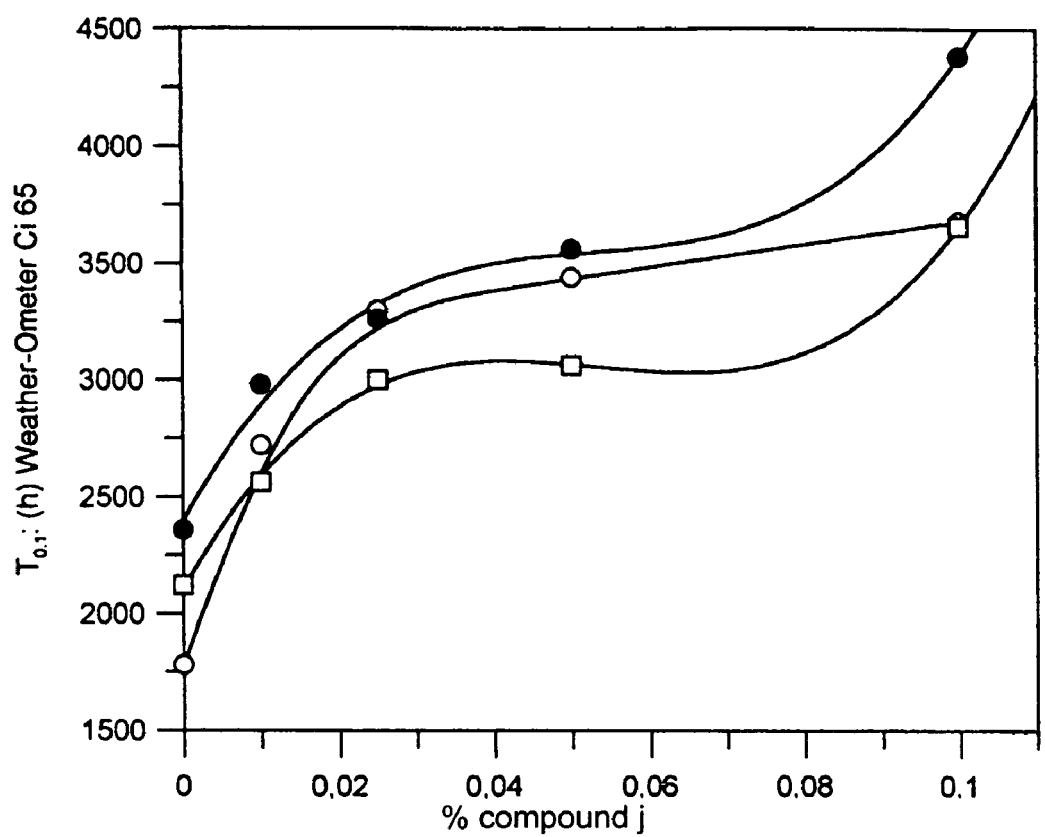
FIG. 2: Effect of the addition of a hydroxyphenyl-triazine UV absorber compound (j) in presence of a polymeric HALS H-3 (white circles), H-4 (white squares) and blend of 1 part H-3 with 1 part H-4 (filled circles) in PP cast films (0.1 mm thick). $T_{0.1}$=exposure time to 0.1 carbonyl absorbance. Example 7.
Figure 3:
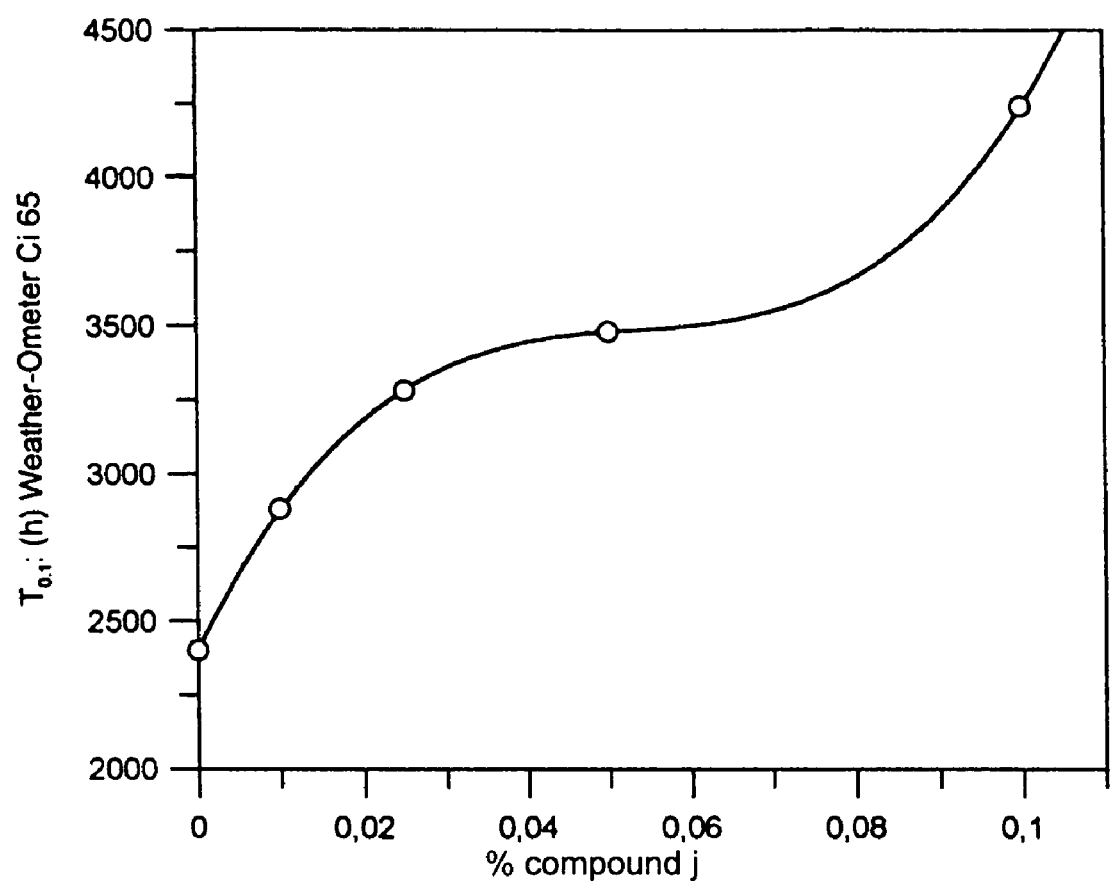
FIG. 3: Effect of the addition of a hydroxyphenyltriazine UV absorber compound j in presence of high molecular mass HALS H-5 in PP cast films (0.1 mm thick). $T_{0.1}$=exposure time to 0.1 carbonyl absorbance. Example 7.
Figure 4:
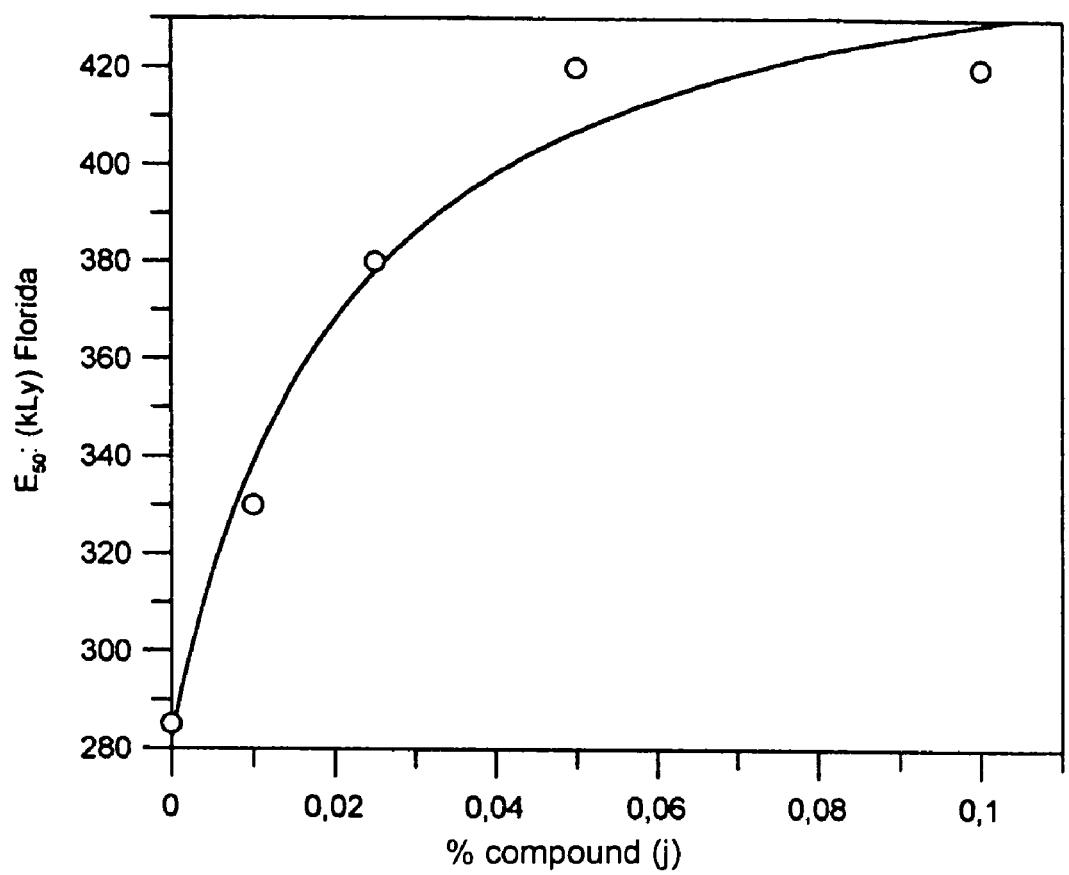
FIG. 4: Effect of the addition of hydroxylphenyl triazine UV absorber (compound j) in presence of 0.1% polymeric HALS H-3 in PP tapes (50 μm thick). E50=energy to 50% retained tensile strength. Example 8.

What is claimed is:

1. Transparent polyolefin article having a thickness between 1 and 200 μm, which is stabilized against the effects of light, oxygen, heat and/or aggressive chemicals by addition of 0.005-0.30% by weight, based on the polyolefin, of a hydroxyphenyl triazine UV absorber selected from the group consisting of

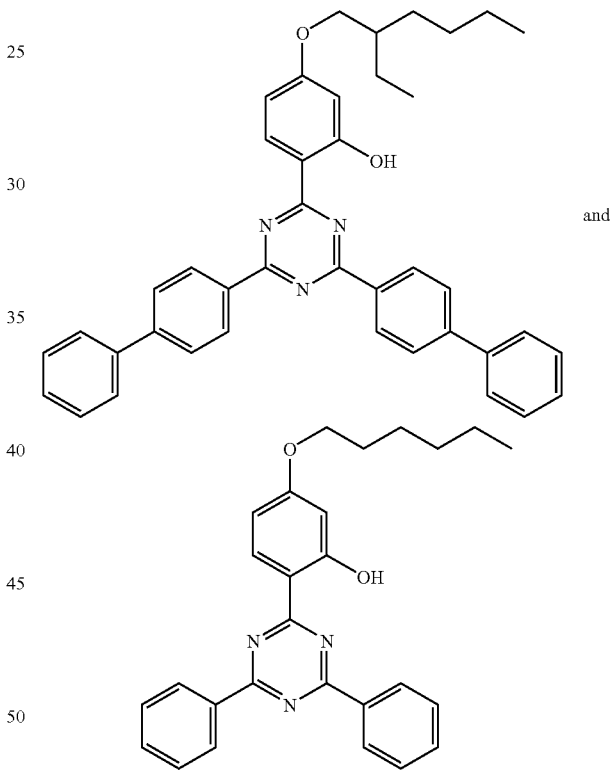

and and containing 0.01 to 6% by weight of the polyolefin, of a sterically hindered amine as further stabilizer, where the hindered amine stabilizer is selected from the group consisting of bis(2,2,6,6-tetramethyl-4-piperidyl)sebacate;
bis(1,2,2,6,6-pentamethyl-4-piperidyl)sebacate;
bis(1,2,2,6,6-pentamethyl-4-piperidyl) n-butyl-3,5-di-tert-butyl-4-hydroxybenzylmalonate;
the condensate of 1-(2-hydroxyethyl)-2,2,6,6-tetramethyl-4-hydroxypiperidine and succinic acid;
a condensate of 1,2-bis(3-aminopropylamino)ethane, 2,4,6-trichloro-1,3,5-triazine and 4-butylamino-2,2,6,6-tetramethylpiperidine;

N,N', N'',N'''-tetrakis(4,6-bis(butyl-(N-methyl-2,2,6,6-tetramethylpiperidin-4-yl)amino)triazin-2-yl)-4,7-diazadecane-1,10-diamine;

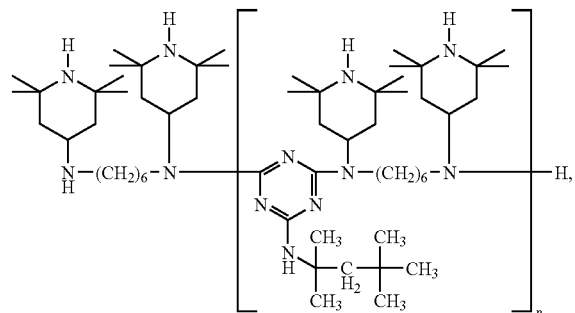

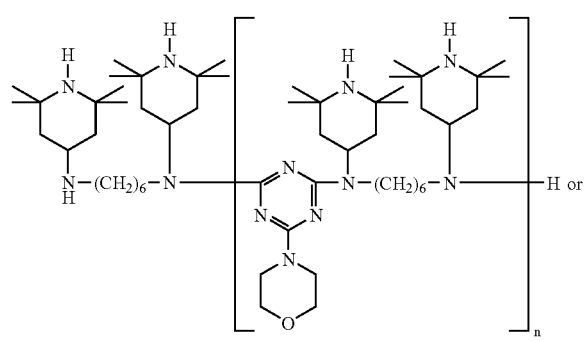

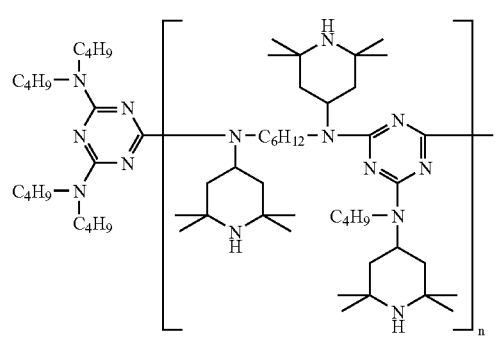

where n is 3-5;

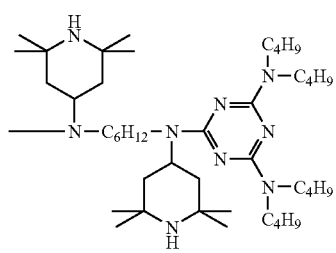

and

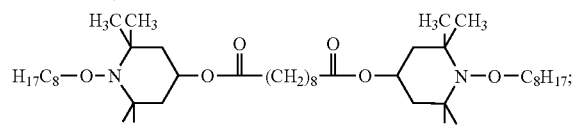

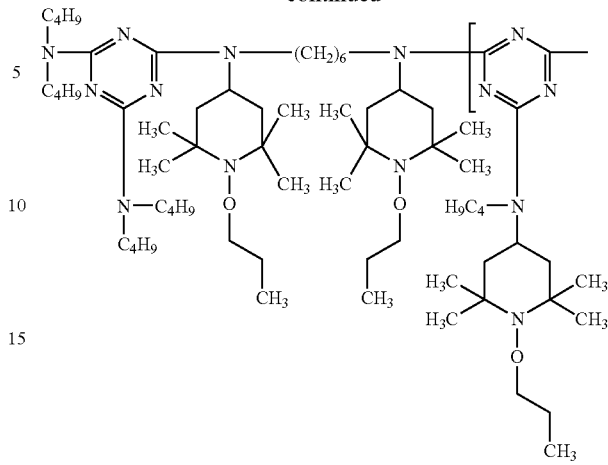

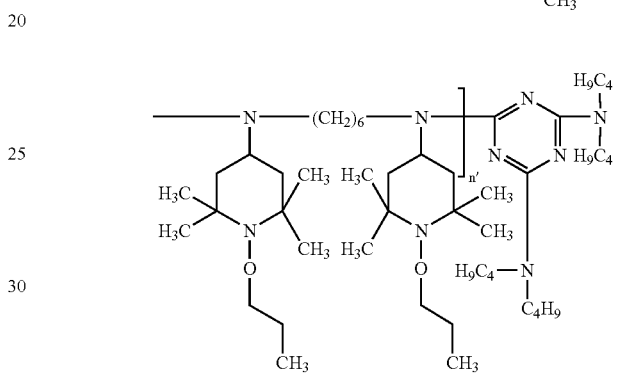

wherein n' is approximately 3.

2. Transparent polyolefin article of claim 1 wherein the weight ratio sterically hindered amine: hydroxyphenyl triazine UV absorber ranges from 2:1 to 20:1.

3. Transparent polyolefin article of claim 1 which is a film, fiber, ribbon or stretched tape.

4. Transparent polyolefin article of claim 3 which is a polyolefin agricultural film.

5. Transparent polyolefin article of claim 1, wherein the polyolefin is polyethylene or polypropylene.

6. Transparent polyolefin article of claim 1 additionally containing a further component selected from the group consisting of processing stabilizers, fillers, clarifiers, modifiers, acid scavengers, flame retardants and further light stabilizers.

7. Transparent polyolefin article of claim 1, where the article contains from 0.005 to 0.15% by weight, based on the polyolefin, of a hydroxyphenyl triazine UV absorber.

8. Transparent polyolefin article of claim 1, where the article contains from 0.005 to 0.06% by weight, based on the polyolefin, of a hydroxyphenyl triazine UV absorber.

9. Transparent polyolefin article of claim 1, where the article contains from 0.01 to 0.06% by weight, based on the polyolefin, of a hydroxyphenyl triazine UV absorber.

10. Transparent polyolefin article of claim 1, where the article contains a further component selected from the group consisting of hindered phenolic antioxidants, hydroxyphenylbenzotriazole or hydroxybenzophenone UV absorbers, phosphites or phosphonites, hydroxylamines and benzofuranones.

11. Transparent polyolefin article of claim 1, where the hydroxyphenyl triazine UV absorber is

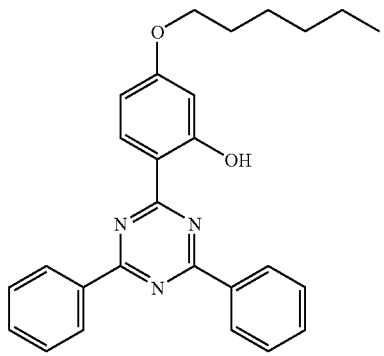

12. Transparent polyolefin article of claim 1, where the hydroxyphenyl triazine UV absorber is

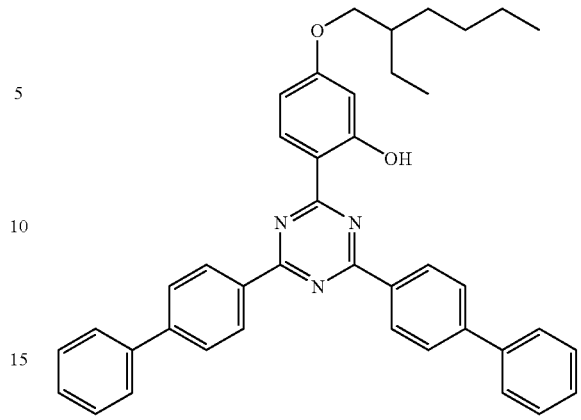

13. Transparent polyolefin article of claim 1, where the hindered amine stabilizer is bis(2,2,6,6-tetramethyl-4-piperidyl)sebacate; the condensate of 1-(2-hydroxyethyl)-2,2,6,6-tetramethyl-4-hydroxypiperidine and succinic acid;

N,N', N'',N'''-Tetrakis(4,6-bis(butyl-(N-methyl-2,2,6,6-tetramethylpiperidin-4-yl)amino)triazin-2-yl)-4,7-diazadecane-1,10-diamine; or

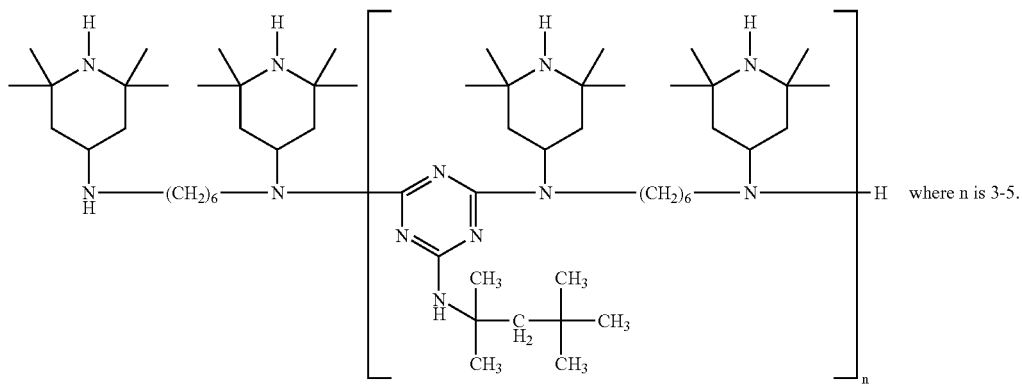

* * * * *